United States Patent [19]

West

[11] Patent Number: 5,045,079
[45] Date of Patent: Sep. 3, 1991

[54] METHOD FOR ALLEVIATING FEMALE URINARY INCONTINENCE

[75] Inventor: Hazel R. West, Elmley Castle, United Kingdom

[73] Assignee: Prosthex Limited, Camberley, United Kingdom

[21] Appl. No.: 538,887

[22] Filed: Jun. 15, 1990

Related U.S. Application Data

[62] Division of Ser. No. 317,475, filed as PCT GB88/00464 on Jun. 15, 1988, abandoned.

[30] Foreign Application Priority Data

Jun. 15, 1987 [GB] United Kingdom ............... 8713938

[51] Int. Cl.$^5$ .............................................. A61F 5/44
[52] U.S. Cl. .................................................. 604/329
[58] Field of Search .................... 604/11, 19, 330, 329, 604/369; 128/898; 600/29

[56] References Cited

U.S. PATENT DOCUMENTS 4,019,498  4/1977  Hawtrey et al. ...................... 600/29

Primary Examiner—Randall L. Green
Assistant Examiner—G. Gualtieri
Attorney, Agent, or Firm—Florence U. Reynolds

[57] ABSTRACT

A cylindrical sponge tampon, soaked in water and then placed in the vagina, supports the urethra to prevent leakage during active movement. The sponge tampon is typically 34 mm in diameter and 60 mm in length when wet and supports a minimum of 0.28 kg (0.5 lb) weight when squashed to half its diameter and not greater than 4.54 kg (10 lbs) per 60 mm length. The preferred material is a formalized polyvinyl alcohol sponge which is a medically proven material.

14 Claims, 4 Drawing Sheets

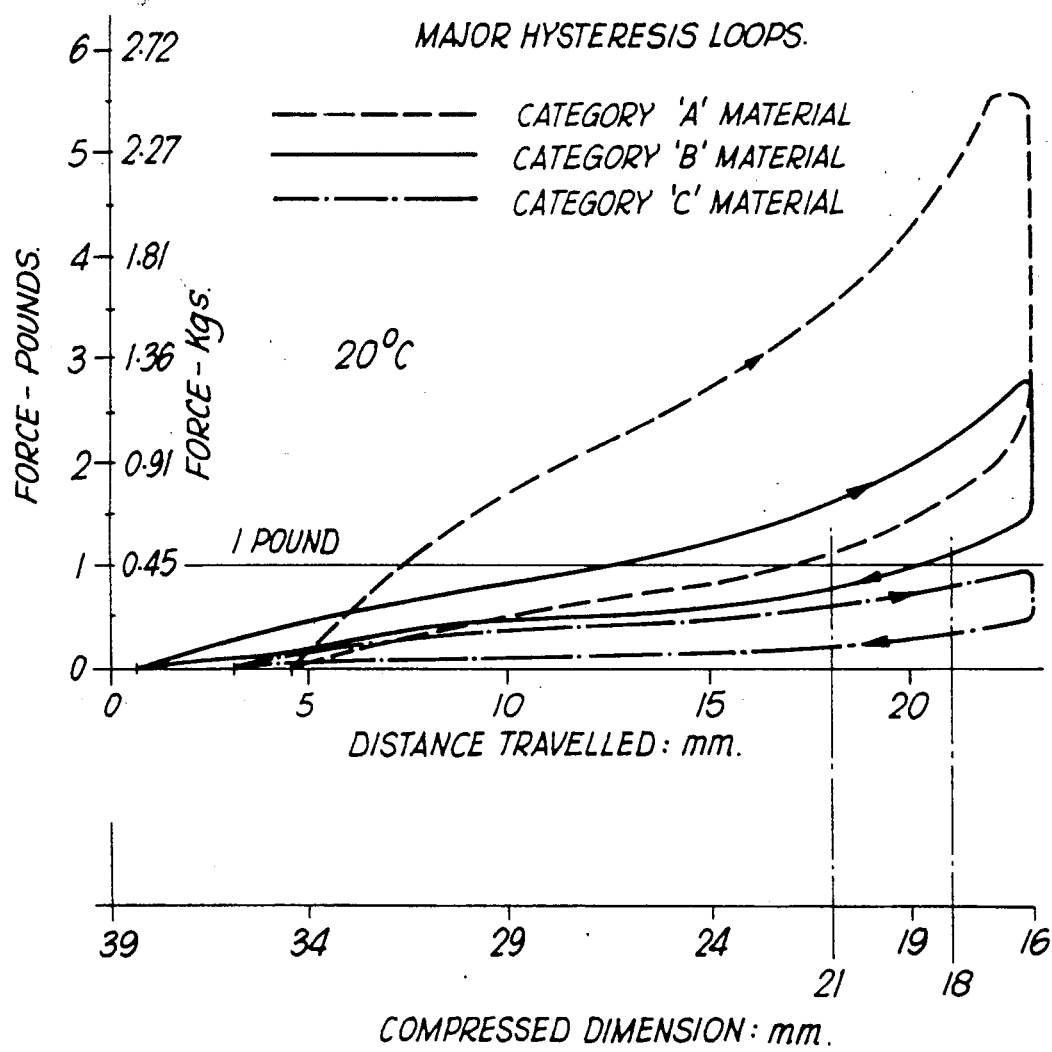

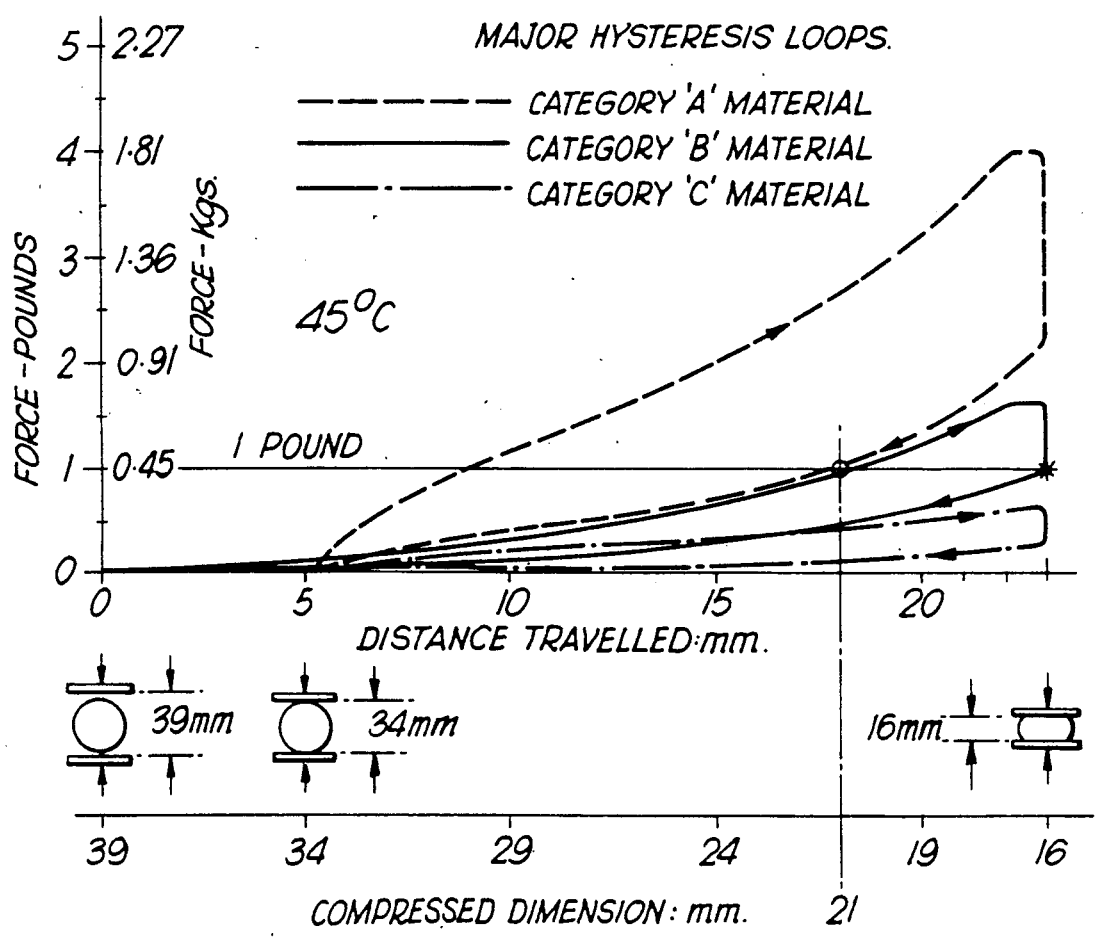

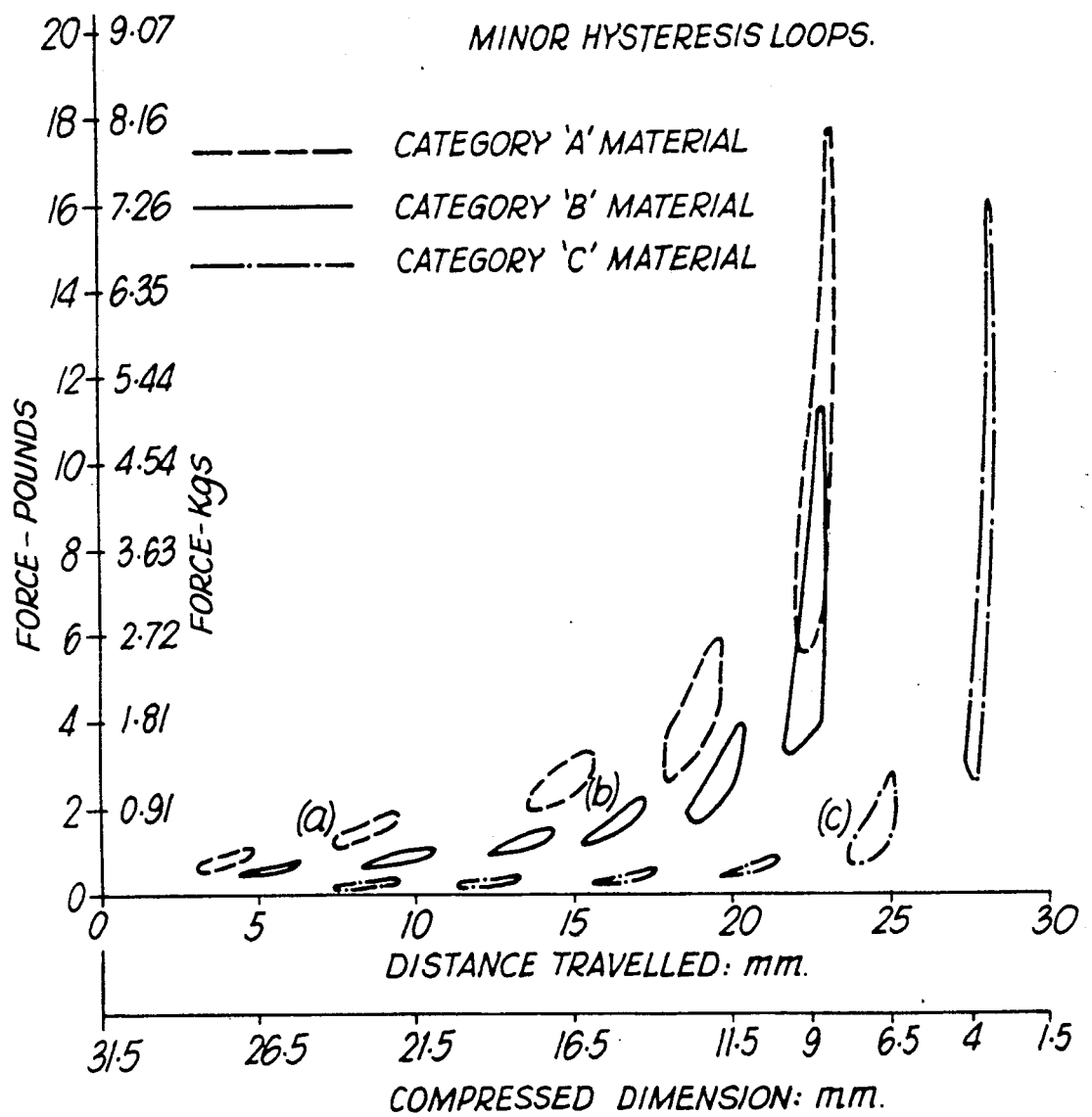

METHOD FOR ALLEVIATING FEMALE URINARY INCONTINENCE

This is a division of application Ser. No. 317,475, filed Feb. 13, 1989, abandoned.

This invention relates to female urinary incontinence devices.

Female urinary incontinence occurs frequently as reported by Thomas et al in the British Medical Journal, 281, p.1243-45 (9 Nov 1980). A postal questionnaire returned by 9,323 women showed that 8.5% aged 15-64, and 11.6% aged 65 and over, suffered regular urinary incontinence. It was also significant that those women who had given birth to children experienced urinary incontinence to a much greater extent than those with no children.

There are several causes of female urinary incontinence:
(1) Perforation of the bladder
(2) Instability causing premature voiding before the bladder becomes full
(3) Retention with overflow due to nervous disorder, and
(4) Stress incontinence The last category is the most common and results from the inability of the muscles to hold the urethra in a closed condition. Stress incontinence can range from mild to severe. Severe cases are usually treated surgically but surgery is not appropriate for mild cases or where the patient is unable to undergo surgery for medical or other reasons.

It has long been known that stress incontinence in females can sometimes be alleviated by the use of support devices within the vagina. Many patents describe specially shaped devices which in some cases are made of sponge or partly of sponge. These devices support the urethra to prevent leakage during such activities as running, walking, jumping, sneezing and coughing.

A cylindrical sponge tampon for use in urinary incontinence and which is similar in size to the internal suppository tampon used extensively during periods, is made by Rocket Ltd. The Rocket tampon has been found to provide limited assistance for a small number of sufferers from urinary incontinence but it cannot assist a much larger number of women who have to wear sanitary towels and waterproof knickers.

Tampons are also used in the treatment of skin disorders of the vagina. For example, U.S. Pat. No. 3,902,493 (Baier and Trokham) describes a medicated tampon having a core of polyurethane foam with a compressibility sufficient only to ensure adequate contact of a medicated surface with the wall of the vagina.

Furthermore, several patents describe rigid or semi-rigid devices specially shaped to press against the wall of the vagina and block the flow of urine through the urethra. These devices are difficult to fit (possibly needing medical assistance) and expensive to manufacture. Moreover, they are also uncomfortable to wear and may cause irritation to the vagina.

The object of this invention is to provide a female urinary incontinence device which gives an adequate degree of support to the urethra but which is easy to insert and remove, comfortable to wear, of low cost, and of medically acceptable material.

According to the present invention there is provided a female urinary incontinence device comprising a tampon of a sponge material which when compressed in the wet state under conditions hereinafter defined is capable of supporting a weight of at least 0.23 kg (0.5 lb) and not greater than 4.54 kg (10 lb) per 60 mm length, the tampon when located in the vagina acting to support the urethra and thereby prevent leakage of urine therefrom during active movement.

The weight supporting capability of the sponge material was determined at 20° C. by compressing a cylinder of sponge material across its diameter of 34 mm between flat plates at a rate of approximately 22 mm per second, allowing a compressed dwell time of 1 minute, and subsequently allowing expansion over a period of 1 second. The above cycle of operations is repeated a further four times with a dwell time in the uncompressed state of 1 second, the measurement being taken on the expansion stroke of the fifth cycle to determine the weight capable of being supported.

Preferably, the material can support a weight of at least 0.45 kg (1 lb) per 60 mm length, and not greater than 2.270 kg (5 lbs) per 60 mm length.

Preferably again, the material is one that maintains its weight supporting capability for long periods of time at body temperature (37.5° C.) and in the presence of urine and vaginal fluids. Further, the sponge material is desirably one that when wet provides the minimum change of force when small changes in compression occur, e.g. 2 mm, due to body movements during walking, running, jumping, coughing and sneezing.

Ideally the tampon should be formed of material which, when compressed to half its diameter between two flat parallel surfaces at a body temperature of 37.5° C., exerts a force of at least 0.45 kg (1 lb) over a period of 12 hours, and also when cycled by 2 mm about this compressed state over a period of 12 hours. A particularly preferred sponge material is a formalized polyvinyl alcohol sponge material made by PROSTHEX LTD., which is a medically proven material. (See Brit. Jnl. Surgery XLII, 618 (1955) and XLIV, 248 (1956).

An embodiment of the invention, together with comparative tests of sponge material, will now be described, by way of example, in relation to the accompanying drawings in which FIG. 1 is a medial vertical section of the female body showing a typically-sized tampon according to the invention in position;

FIGS. 3 and 4 are graphs of the major hysteresis loops of force against distance for various wet tampons of the size shown in FIG. 2 at 20° C. and at 45° C. respectively; and FIG. 5 is a graph of the minor hysteresis loops of force against distance for various wet tampons of the FIG. 2 size at 20° C.

Figure 1:
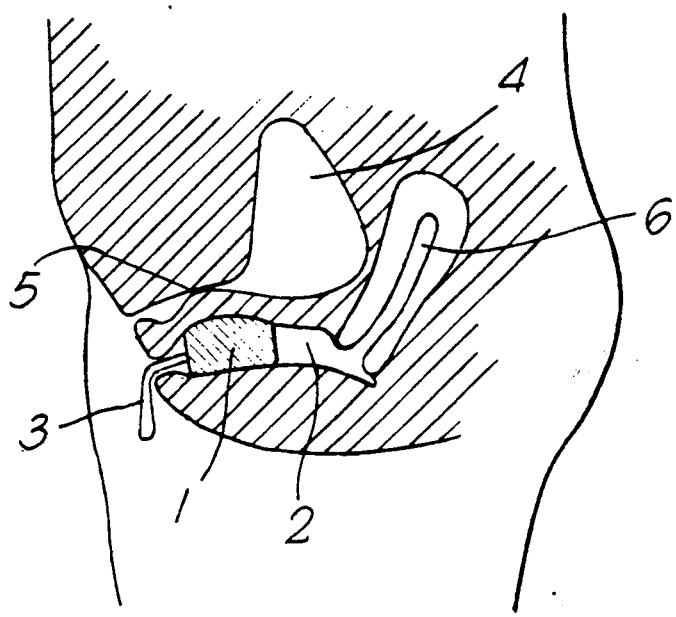

FIG. 1 shows a cylindrical tampon 1 of typical size in position in a vagina 2 and having a loop of string 3 attached thereto and protruding from the vagina to allow easy removal of the tampon 1. The bladder 4 empties via the urethra 5 and the tampon 1 helps to keep the urethra 5 in a closed condition. The uterus 6 is also shown.

Figure 2:
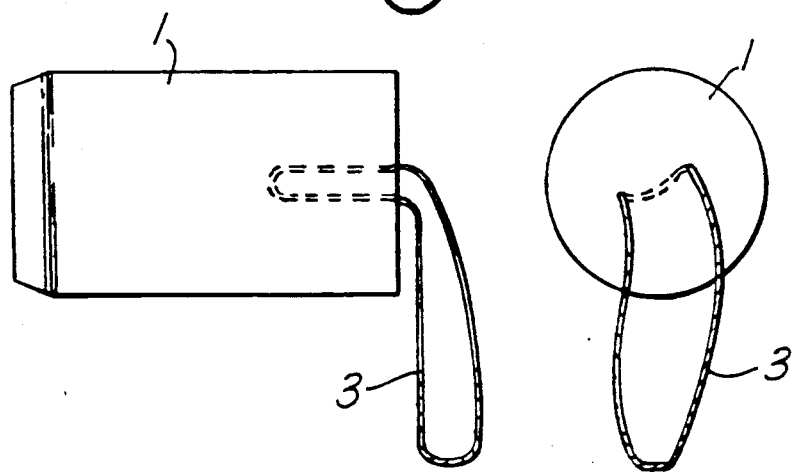
FIG. 2 is a detailed side and end elevation of the tampon of FIG. 1.

FIG. 2 shows the typically-sized tampon 1 having a diameter of 34 mm and length of 60 mm: it may have as shown a slightly reduced diameter at the end remote from the loop 3 to facilitate fitment. Several sizes of tampon (possibly three) are required to suit the range of physical sizes of the vagina. The length is more important and may range from 40 to 80 mm whereas the diameter is less critical and may range from 30 to 38 mm. All these sizes apply in the wet condition.

The selection of sponge material of which the body of the tampon 1 is formed will now be discussed in detail.

FIGS. 3 and 4 show, graphically, the hysteresis loops of cylinders of wet sponge material of typical size (34 mm) and various types when compressed across their diameters between flat plates. This test approximately replicates the compressive force applied to the tampon when in position in the vagina. The tests were carried out with the cylinder in a moist condition at both 20° C. (FIG. 3) and 45° C. (FIG. 4). 45° C. was chosen for test purposes so as to slightly exceed body temperature (37.5° C.) to allow a safety factor as test conditions were not easy to control (±5° C. estimated).

The hysteresis loops were taken in general accordance with the previously defined conditions as follows:

Each compression took place over a period of approximately 1 second, i.e. the rate of movement was approximately 22 mm per second. The tampon was then held in a compressed state for various periods of time up to 30 minutes in duration, following which expansion took place over a period of approximately 1 second. Recompression of the tampon to perform a further hysteresis loop was made after a 1 second dwell time in the uncompressed state.

It was found that a reasonably stable hysteresis loop was obtained after five cycles, each with a compressed dwell time of 1 minute in the case of the tests at 20° C. The procedure for the tests at 45° C. was slightly modified to allow for cooling of the water bath in which the test sponge was immersed in that the sponge was initially held compressed for five minutes in water at an initial temperature of 50° C., and then cycled five times with a dwell time in the compressed state of only 5 seconds. The curves shown in FIGS. 3 and 4 relate to the final (fifth) cycle which, of course, exhibits values substantially lower than those of the first cycles. It is believed that the lower curve portion of the fifth cycle represents a reasonable measure of the performance of the tampon in practice.

A range of different polyurethane and cellulose sponge materials was tested to assess their suitability for use in the present invention and were divided into three categories:

| A | Preferred - provided support for most situations |
| B | Useful - provided support for some situations |
| C | Unsuitable - provided inadequate support |

Typical samples from these three categories were tested to measure the support force against distance, and the results are shown in FIGS. 3 and 4, the category A material exhibiting the highest support capability, category B intermediate capability, and category C the lowest capability.

After a period of time under pressure, the sponge force was generally at or close to the lower portion of its hysteresis curve, i.e. the curve obtained during the release of pressure shown by the arrows pointing to the left in FIGS. 3 and 4.

Assuming that 0.45 kg (1 lb) force is required to provide adequate support for most situations, it will be seen that the following compressed dimensions are necessary:

|   | 20° C. | 45° C. |
| --- | --- | --- |
| A | 21 mm | 21 mm |
| B | 18 mm | 16 mm |
| C | — | — |

Category A material easily achieves the 0.45 kg (1 lb) force.

Category B material is adequate at 20° C. and just achieves 0.45 kg (1 lb) at 16 mm compressed dimension at 37.5° C. (body temperature).

It is therefore seen that the sponge in category C is not capable of providing a 0.45 kg (1 lb) force when limited to a 16 mm compressed dimension (separate tests have shown that compression to less than 5 mm would be necessary), and it is not therefore suitable for use in the present invention.

The sponge material of which the previously-mentioned Rocket tampon is formed falls into category C.

The polyurethane foam material used in forming the tampon of U.S. Pat. No. 3,902,493 has a wet modulus of compressibility of foam 70.31 kg/m$^2$ (0.1 psi) to 210.93 kg/m$^2$ (0.3 psi) according to ASTM D 1564. Experience with such polyurethane foams has shown that such a material exerts only a small force when released from compression and that when tested under test conditions of the present invention would fall into Category C.

It is also important that the maximum force required to compress the tampon should not be excessive to permit ease of insertion into the vagina. The tampon would ideally require less than 2.27 kg (5 lbs) force to compress it to half its diameter, while a maximum force of 4.54 kg (10 lbs) is marginally acceptable.

FIG. 5 gives the results of tests to show the effect of small movements on the support force.

The curves shown in FIG. 5 are known as minor hysteresis loops and are obtained by compressing the sponge to a given point on the hysteresis curve then partly relaxing the compression by a small amount (2 mm). Several cycles round this minor loop are taken to stabilise it at its lowest level at which time a measurement is taken. Compression and relaxation of the sponge is effected in approximately 0.25 seconds to simulate rapid body movement.

It can be seen that the minor loops lie almost horizontally at low compressions, i.e. only a small change in force occurs for the 2 mm change in compression.

For large compressions, the minor loops become almost vertical, i.e. a large change in force occurs for the 2 mm change in compression. A highly compressed tampon is therefore unsatisfactory in practice as only a small dimensional change will result in a large loss in compressive force. Thus running, jumping, bending or even walking could cause enough movement to release the compressive force.

Three particular minor loops in FIG. 5 are labelled (a), (b) and (c) and correspond with the sponge materials A, B and C. These three minor loops have similar mean values of pressure around 1.5 pounds (0.68 kg). However, for the 2 mm change of compression the three categories of material show widely different reductions in pressure:

| Material | | Reduction in Pressure | |
| --- | --- | --- | --- |
| Category | Minor Loop | Pounds | Kg |
| A | (a) | 0.8 | 0.36 |

| Material Category | Minor Loop | Reduction in Pressure | |
|---|---|---|---|
| | | Pounds | Kg |
| B | (b) | 1.2 | 0.54 |
| C | (c) | 2.4 | 1.08 |

Category C material has three times the change of pressure of Category A material, whilst Category B material is only 50% higher.

The size of the tampon is governed primarily by what is easy and convenient to fit in place and, moreover, by what is comfortable in use. This size will thus vary with each person. However, although a tampon that is easily compressible will obviously be somewhat easier to fit, it will need to remain in an extremely compressed state in order to provide adequate support thus leading to an excessive change of compressive force, with small deflections. At the other extreme, a rigid tampon will be extremely uncomfortable and will not yield to conform to the required internal shape so as to apply relatively constant pressure equally over the area in question.

It is preferred that the tampon be left in place during the day, it being quite unnecessary to remove it when urinating. However, it should be removed at night, and washed thoroughly. Obviously for hygienic reasons it should be used only for a few days before being discarded. This also helps to guard against the very rare phenomenon of toxic shock. The requirements for day long wear and frequent renewal demand that the tampon should be of medically proven material but at the same time be of low cost and capable of being made by an economic production process.

Sponge materials are generally of polyurethane or cellulose and a wide range of such commercially available materials were tested in the search for a suitable tampon material giving adequate support. None was found to be satisfactory. Experience with the three categories of tampon sponge material has in fact shown not only the ideal material is in category A as described above, but also that the only material which adequately conforms to the requirements of category A is a polyvinyl formal sponge produced by Prosthex Ltd. from polyvinyl alcohol by the action of formaldehyde by a process which yields a cross-bonded polymer having great physical and chemical stability. The sponge is a medically proven material which has been found to be reasonably comfortable for all-day use; impervious to attack by body fluids, in particular urine and vaginal secretions; and to maintain its shape and resilience for long periods. It should be noted that the polyvinyl formal sponge material has a rigid cylindrical shape when completely dry and should be soaked in warm water immediately prior to use. The size of the sponge when dry is smaller than when wet. (It will have been noted that the sizes quoted in this specification all relate to the size when wet.)

I claim:

1. A method for alleviating female urinary incontinence which comprises the steps of providing a tampon of a sponge material which, when compressed in the wet state is capable of supporting a weight of at least 0.23 kg (0.5 lb) and not greater than 4.54 kg (10 lb) per 60 mm length, soaking said tampon in water, and inserting said water-soaked tampon in the vagina, thereby supporting the urethra and preventing leakage from the urethra during active movement, the weight supporting capability of the sponge material being determined at 20° C. by compressing a cylinder of sponge material across its diameter of 34 mm between flat plates at a rate of approximately 22 mm per second, allowing a compressed dwell time of 1 minute, and subsequently allowing expansion over a period of 1 second, repeating the above cycle of operations a further four times with a dwell time in the uncompressed state of 1 second, and taking a measurement on the expansion stroke of the fifth cycle to determine the weight capable of being supported.

2. The method as claimed in claim 1, comprising the step of selecting a material for the tampon which is capable of supporting a weight of at least 0.45 kg (1 lb) per 60 mm length.

3. The method as claimed in claim 1, comprising the step of selecting a material for the tampon which is capable of supporting a weight not greater than 2.270 kg (5 lbs) per 60 mm length.

4. The method as claimed in claim 1, comprising the step of selecting a material for the tampon which is capable of substantially maintaining its supporting force under conditions of transient movement during a period of one second or less.

5. The method as claimed in claim 1, comprising the step of providing a tampon which is of generally cylindrical shape and is from 30 to 38 mm in diameter and from 40 to 80 mm in length in the wet expanded state.

6. The method as claimed in claim 1, comprising the step of selecting a material for the tampon which when cycled by 2 mm about said compressed state, exerts a force of at least 0.45 kg (1 lb) over a period of 12 hours.

7. The method as claimed in claim 1, comprising the step of selecting a formalized polyvinyl alcohol sponge material as the material for the tampon.

8. The method as claimed in claim 2, comprising the step of selecting a material for the tampon which is capable of substantially maintaining its supporting force under conditions of transient movement during a period of one second or less.

9. The method as claimed in claim 2, in which the material, when cycled by 2 mm about said compressed state, exerts a force of at least 0.45 kg (1 lb) over a period of 12 hours.

10. The method as claimed in claim 3, comprising the step of selecting a formalized polyvinyl alcohol sponge material as the material for the tampon.

11. The method as claimed in claim 4, comprising the step of selecting a formalized polyvinyl alcohol sponge material as the material for the tampon.

12. The method as claimed in claim 5, comprising the step of selecting a formalized polyvinyl alcohol sponge material as the material for the tampon.

13. The method as claimed in claim 6, comprising the step of selecting a formalized polyvinyl alcohol sponge material as the material for the tampon.

14. The method as claimed in claim 12, comprising the step of selecting a formalized polyvinyl alcohol sponge material as the material for the tampon.

* * * * *